United States Patent [19]
de Jong

[11] Patent Number: 5,213,242
[45] Date of Patent: May 25, 1993

[54] STORAGE DEVICE FOR AN IMPLANTING TOOL

[75] Inventor: Hendrik J. de Jong, Groenlo, Netherlands

[73] Assignee: N.V. Nederlandsche Apparatenfabriek Nedap, De Groenlo, Netherlands

[21] Appl. No.: 625,659

[22] Filed: Dec. 12, 1990

[30] Foreign Application Priority Data

Dec. 14, 1989 [NL] Netherlands .......................... 8903068

[51] Int. Cl.⁵ .......................... A45C 13/30; A45F 3/14
[52] U.S. Cl. .......................... 224/222; 224/232; 269/95
[58] Field of Search ............... 224/222, 232, 233, 242, 224/245, 904, 921, 226, 247; 119/174; 604/57, 59, 60, 61, 62; 606/116, 117; 40/300, 301, 302, 303, 304; 206/214, 224, 363, 371, 372; 81/9.22; 269/95, 287

[56] References Cited

U.S. PATENT DOCUMENTS

| 327,759 | 10/1885 | Boyle | 224/222 X |
|---|---|---|---|
| 1,701,057 | 2/1929 | Thatcher | 224/247 X |
| 1,812,302 | 6/1931 | Nies | 224/233 |
| 2,525,398 | 10/1950 | Collins | 224/222 X |
| 2,640,596 | 6/1953 | Reeder | 211/87 |
| 2,755,772 | 7/1956 | Palmer | 224/222 |
| 2,854,134 | 9/1958 | Humphrey | 206/57 |
| 2,858,044 | 10/1958 | Schadenburg | 221/46 |
| 3,199,754 | 8/1965 | Sorensen | 224/5 |
| 3,346,152 | 10/1967 | Geisendroff | 224/5 |
| 3,430,760 | 3/1969 | Ulmer | 224/242 X |
| 3,744,623 | 7/1973 | Woofter | 206/19.5 R |
| 4,263,910 | 4/1981 | Pardekoopes et al. | 604/60 |
| 4,500,019 | 2/1985 | Curley, Jr. | 224/222 |
| 4,746,042 | 5/1988 | King | 224/148 |
| 4,846,793 | 7/1989 | Leonard et al. | 604/62 |
| 4,848,624 | 7/1989 | Clen | 224/222 |
| 4,913,326 | 4/1990 | Echelson | 224/222 |
| 4,951,857 | 8/1990 | Carr | 224/242 X |
| 5,024,361 | 6/1991 | Flowers | 224/904 X |

Primary Examiner—Henry J. Recla
Assistant Examiner—Glenn T. Barrett
Attorney, Agent, or Firm—Jacobson, Price, Holman & Stern

[57] ABSTRACT

A storage device for an implanting tool for implanting an implant into the body of an animal, the implanting tool having a handle (16) provided with a hollow needle (4) and being loadable by inserting the needle into an implant storage cavity (6) of a reservoir (2) for implants, including a holder portion (8, 9, 11) for holding the reservoir (2) and a fastening device (12, 13, 14) for fastening the storage device in an operative position, the fastening device and holder portion being so shaped, and so positioned relative to each other, that, in the operative position of the storage device, a cavity of a reservoir placed in the holder portion can hold the needle of an implanting tool.

7 Claims, 2 Drawing Sheets

STORAGE DEVICE FOR AN IMPLANTING TOOL

BACKGROUND OF THE INVENTION

This invention relates to a storage device for an implanting tool for implanting an implant into the body of an animal, said implanting tool including a handle provided with a hollow needle, and being loadable by inserting said needle into an implant accommodating cavity of a reservoir for implants.

An implanting tool of this kind often includes an elongate body, for example of cylindrical shape, from which an injection needle projects at one end. An example of such a pen-shaped implanting tool, sometimes called an implanting pen, is described in applicants' prior Netherlands patent application No. 8902186. The prior patent application also shows a reservoir in which a number of implants (e.g. 10 implants), can be accommodated under sterile conditions. An implant includes a capsule, often of cylindrical shape, and containing, for example, a medicine or an identification chip.

For considerations of efficiency, the implantation should preferably be done by one person, the implanter. A complete implanting operation includes two steps, namely, catching and positioning the animal in question, and then the implantation proper. The implanter needs both hands for catching and positioning the animal, and also for the implantation itself by means of an implanting pen and a loose reservoir containing implants. After the implanting operation, both the reservoir and the implanting pen must be carefully put down at a safe and clean place in order that a next animal may be caught and positioned. When that has been done, the implanting tool must be handed to the implanter by another person, or he must get hold of it himself. In the first case, a second person is needed. In the second case, there are also objections, for example, in connection with the speed with which a series of implants can be introduced, or in connection with the risk of dropping the tool, so that it is contaminated. Furthermore, the tool is vulnerable i.e. it is liable to be damaged.

BRIEF SUMMARY OF THE INVENTION

It is an object of the present invention to provide a solution for the above problems, to the effect that one person can perform all operations, so that cost will be minimized.

More in general, it is an object of the invention to provide a storage device for an implanting tool which is easy and efficient to use in practice.

According to the present invention, therefore, there is provided a storage device of the above kind which is characterized by a holder portion for accommodating a reservoir for implants and by fastening means for fastening the storage device in the operative position, said fastening means and said holder portion being so shaped, and so positioned relative to each other that, in the operative position of the storage device, a cavity of a reservoir placed in the holder portion can hold the needle of an implanting tool.

BRIEF DESCRIPTION OF THE DRAWINGS

Further features and advantages of the invention will become apparent from the following description, read with reference to the accompanying diagrammatic drawings, wherein.

DETAILED DESCRIPTION

Figure 1:
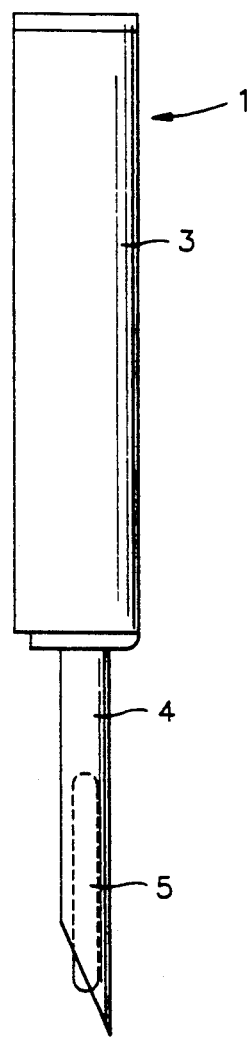
FIG. 1 shows an example of an implanting tool of the prior art.
Figure 2:
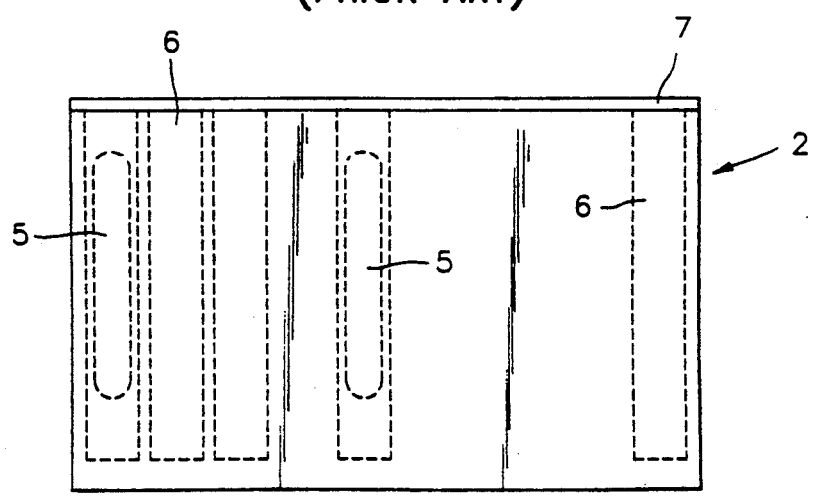
FIG. 2 shows an example of a prior art reservoir for implants, for use with the tool shown in the FIG. 1.

FIGS. 1 and 2 illustrate schematically an embodiment of an implanting pen 1 and a reservoir 2 for implants, respectively, as described in the above prior Netherlands patent application 89 02186. As shown, the implanting pen in this example has a cylindrical handle 3 which is provided with an implanting needle 4. Prior to an implanting operation, the needle is provided with an implant 5. A number of implants, for example, 10, are accommodated in reservoir 3. The reservoir has cavities 6 for receiving the implants. Cavities 6 are sealed with a foil 7. The implants are sterile to prevent infection. For this purpose, the cavities may be filled with an antiseptic paste or liquid. The implanting pen is loaded by sticking needle 4 through foil 7. In the manner described in the prior Netherlands patent application 89 02186, implant 5 is thus loaded into the needle, whereafter the implanting pen is suitable for an implanting operation. As stated before, the implanter uses both hands, one to hold the reservoir and one to hold the implanting pen, and should thereafter carefully put away both the reservoir and the pen to catch and position an animal.

Figure 3:
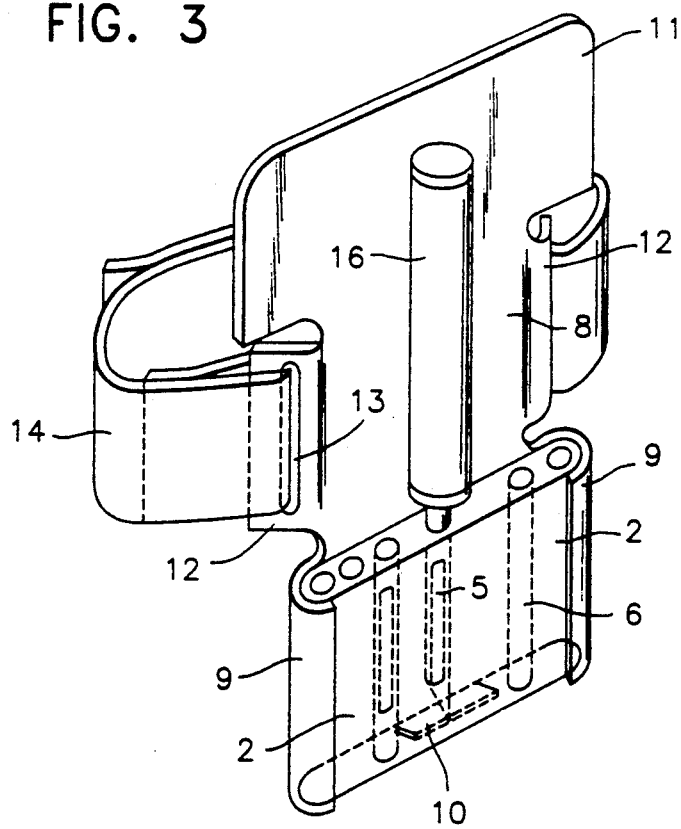
FIG. 3 is a perspective schematic view of an embodiment of a storage device according to the present invention.

FIG. 3 shows schematically and in perspective view an embodiment of a storage device according to the present invention. In the embodiment shown, the device is designed to be fastened around the arm, e.g., the upper arm of the implanter (user). It is also possible, however, for the storage device according to the invention to be so designed that it is suitable to be fastened to the implanter's leg or body, or for it to be secured to a wall.

The embodiment shown in FIG. 3 comprises a base plate 8 with two forwardly extending parts 9 between which a reservoir 2 can be slid into contact with a stop 10. Parts 9 are preferably so shaped and/or positioned that the reservoir is held in a somewhat clamped fashion. At the end opposite the stop, base plate 8 has a part 11 extending beyond parts 9, and further includes two bent lips 12 each provided with a slot 13. Through these slots 13, a strap or strip 14 can be inserted and fastened at one side in known manner. The strap can be provided in known manner with a buckle or bur fastener, such as teazle strips, for example, and Velcro strips (trademark) to adjust the length of the strap for it to fit comfortably around the desired part of the implanter's body. Naturally, other fastening methods, such as by means of elastic are conceivable.

The portion 11 functions as a guard for the implanting tool 16, for example, to prevent it from being pushed away by folds of the implanter's clothing.

The procedure during the implanting operation is as follows. The implanter fastens the storage device, for example, around his upper arm, and slides a reservoir 2 containing implants 5 into the holder formed by plate 8 and parts 9. He grips the implanting pen and pushes the needle from the top into a cavity 6 which contains an implant 5. The foil 7 is thus pierced, and the implant is taken up into needle 4. The needle is inserted so deeply into the reservoir cavity that the implanting pen cannot fall, and that an implant is taken up within the needle. Accordingly, the implanting tool is placed in a stand-by position and loaded in one operation. In the embodiment shown, the implanting tool is supported exclusively by the needle inserted into the reservoir. The tool handle is substantially free from the base plate 8. The implanter now has his hands free to catch an animal and place it into a proper position for implantation. He then takes the loaded implanting pen out of the reservoir, and thus the implanting tool out of the storage device, and implants the implant into the animal. The animal is then released and can walk away, and the implanter pushes the implanting pen into another cavity 6 of reservoir 2, which is filled with an implant. He is then ready for another cycle of catching, positioning an animal and implanting the implant.

Figure 4:
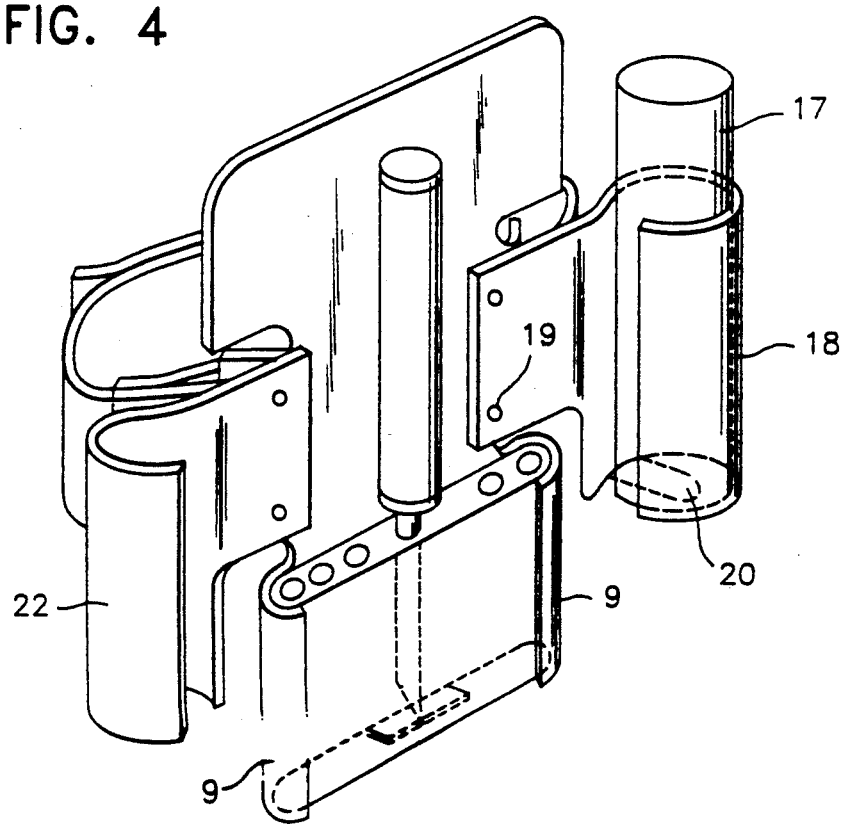
FIG. 4 is a view similar to FIG. 3 showing a variant of the embodiment illustrated in FIG. 3.

In some cases, after the implantation, the animals are released in the same pen or cage. In that case it may be of advantage for the animals to be marked after the implantation. For the storage of a suitable marker 17 with a suitable dye, the storage device according to the invention can be extended with a suitable holder 18, as shown in FIG. 4. Holder 18 may be formed out of base plate 8, or attached to it, for example, with rivets 19. A lip 20 at the bottom prevents the marker 17 from falling out of holder 18.

In some cases, the storage device according to the invention can of course be fastened elsewhere to the implanter's body or clothing, or, for example, to a wall, stall barrier or chair leg. The fastening means should then, where necessary, be adapted. Thus, for example, fastening may be effected with screws or with a clamping device. In all cases, the implanter has both hands free during certain moments of the implanting process, while the implanting tool is safely stored.

It is observed that, after reading the foregoing, various modifications will readily occur to those skilled in the art. Thus, in the embodiment shown, portion 11 of the base plate is provided with rearwardly bent lips 12, which each have a slot 13 through which a piece of belt extends. However, the lips may alternatively be provided at the level of the portion holding the reservoir 2, or even be omitted altogether and replaced by two slots. Futhermore, a belt or fastening strip consisting of two parts can be used, but also a belt or strip consisting of a single part. In the latter case, one or two lips drawn outside the plane of the base plate can serve to receive the belt or strip as a kind of tag.

The base plate may be made of any suitable material, for example, metal or synthetic plastics. In the latter case, reinforcing ribs may be used. Also, the belt or fastening strip may be formed integrally with a plastic plate.

In the embodiment shown, the bent parts 9 are edge portions of the base plate. Alternatively, however, the parts 9 may be loose members secured to the base plate in some suitable manner. Also, parts 9 may each be formed of a number of suitably shaped lips and/or each be provided with a stop corresponding to stop 10, and optionally in combination with stop 10. Parts 9 may also be provided with fastening means for the belt or fastening strip 14.

The shape of parts 9 should of course be adapted to the reservoirs to be used.

A reservoir could be provided with a special cavity adapted to receive the needle of an implanting tool in situations in which it is not (yet) desirable for the implanting tool to be loaded with an implant. For a similar purpose, base plate 8 and/or part 11 thereof could be provided with a special holder similar to the marker holder 22 shown at 18, but then further provided with a sheath for protection of the needle.

The above and similar modifications are considered to fall within the scope of the present invention.

We claim:
1. A holding device for holding a reservoir and an implanting tool, the reservoir having cavities containing implants and the implanting tool having a handle and a hollow needle loadable by inserting said needle into one of said cavities containing an implant to insert an implant into said needle, the holding device comprising:
  a base plate having a front side, a back side, a first portion, a second portion extending substantially above said first portion when said holding device is in position for use, and opposite side edge regions on said second portion;
  reservoir retaining members in relative spaced relationship protruding substantially outwardly from said front side of said first portion of said base plate and having a shape for receiving and releasably retaining said reservoir on said base plate so that said cavities are accessible during use of said holding device;
  a lip on each of said opposite side edge regions;
  a slot in each lip; and
  fastening means mounted on said lips and engaging said slots for fastening said holding device on an object in a position for use with said second portion of said base plate substantially above said first portion, so that when a reservoir is retained on said base plate by said retaining members and said needle of said implanting tool is inserted in one of said cavities of said reservoir, said handle of said implanting tool extends adjacent to said front side of said second portion of said base plate whereby said second portion serves as a guard plate for said handle when the holding device is in position for use.

2. The holding device as claimed in claim 1 wherein:
  said fastening means comprises at least one releasable strap means for fastening around a part of a user's body.

3. The holding device as claimed in claim 1 wherein:
  said lips are bent relative to said base plate toward said back side of said base plate.

4. The holding device as claimed in claim 1 and further comprising:
  at least one stop member protruding substantially outwardly from said front side of said first portion of said base plate between said reservoir retaining members for engaging a part of said reservoir when said reservoir is retained in said retaining members.

5. The holding device as claimed in claim 1 and further comprising:
  an additional marker holder member mounted on said second portion of said base plate adjacent one of said side edge regions and extending substantially outwardly from said front side for receiving and releasably holding a marker.

6. The holding device as claimed in claim 1 and further comprising:
  a first additional holder portion mounted on said second portion of said base plate adjacent one of said side edge regions and extending substantially outwardly from said front side for receiving the implanting tool when not inserted in a cavity of said reservoir.

7. The holding device as claimed in claim 6 and further comprising:

an additional marker holder member mounted on said second portion of said base plate adjacent the other of said side edge regions and extending substantially outwardly from said front side for receiving and releasably holding a marker.

* * * * *

UNITED STATES PATENT AND TRADEMARK OFFICE
CERTIFICATE OF CORRECTION

PATENT NO. : 5,213,242
DATED : May 25, 1993
INVENTOR(S) : Hendrik Johannes de Jong and Ebele Marten Postma It is certified that error appears in the above-identified patent and that said Letters Patent is hereby corrected as shown below:

On the title page, item [75], insert --Ebele Marten Postma-- as a joint inventor.

Signed and Sealed this

Fourteenth Day of December, 1993

Attest:

BRUCE LEHMAN

*Attesting Officer*    *Commissioner of Patents and Trademarks*